(12) United States Patent
Levin

(10) Patent No.: US 10,485,639 B2
(45) Date of Patent: Nov. 26, 2019

(54) VIEWFINDER WITH REAL-TIME TRACKING FOR INTRAORAL SCANNING

(71) Applicant: Align Technology, Inc., San Jose, CA (US)

(72) Inventor: Adi Levin, Nes Tziona (IL)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 15/974,072

(22) Filed: May 8, 2018

(65) Prior Publication Data
US 2019/0008616 A1 Jan. 10, 2019

Related U.S. Application Data

(63) Continuation of application No. 15/645,243, filed on Jul. 10, 2017, now Pat. No. 9,987,108, which is a
(Continued)

(51) Int. Cl.
*A61C 9/00* (2006.01)
*A61B 1/00* (2006.01)
*A61B 1/24* (2006.01)

(52) U.S. Cl.
CPC ........ *A61C 9/0053* (2013.01); *A61B 1/00045* (2013.01); *A61B 1/24* (2013.01)

(58) Field of Classification Search
CPC ...... A61C 9/0053; A61B 1/00045; A61B 1/24
(Continued)

(56) References Cited

U.S. PATENT DOCUMENTS

| 2,467,432 A | 4/1949 | Kesling |
| 3,407,500 A | 10/1968 | Kesling |

(Continued)

FOREIGN PATENT DOCUMENTS

| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.
(Continued)

*Primary Examiner* — William C Vaughn, Jr.
*Assistant Examiner* — Jae N Noh
(74) *Attorney, Agent, or Firm* — Wilson Sonsini Goodrich & Rosati

(57) ABSTRACT

Methods and systems for scanning an intraoral cavity of a patient provide capturing one or more viewfinder images of the intraoral cavity and scanning the intraoral cavity with an intraoral scanner to generate one or more topography scans of the intraoral cavity. The one or more topography scans may correspond to the one or more viewfinder images. The methods and systems further provide capturing a viewfinder image of a portion of the intraoral cavity, the viewfinder image overlapping with the one or more viewfinder images. An area of overlap of the viewfinder image with the one or more viewfinder images can be determined. One or more indicators of the area of overlap can be displayed on one or more locations of a display in order to provide guidance for positioning a field of view of the intraoral scanner.

20 Claims, 10 Drawing Sheets

Related U.S. Application Data continuation of application No. 14/463,464, filed on Aug. 19, 2014, now Pat. No. 9,724,177.

(58) Field of Classification Search
USPC .......................................................... 348/66
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Shishti et al. |

(56) References Cited

U.S. PATENT DOCUMENTS

| | | | |
|---|---|---|---|
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 7,286,954 | B2 | 10/2007 | Kopelman et al. |
| 7,424,218 | B2 | 9/2008 | Baudisch et al. |
| 7,885,440 | B2 | 2/2011 | Fram et al. |
| 7,890,290 | B2 | 2/2011 | Kopelman et al. |
| 8,207,964 | B1 | 6/2012 | Meadow et al. |
| 8,217,989 | B2 | 7/2012 | Kim et al. |
| 8,330,831 | B2 | 12/2012 | Steinberg et al. |
| 8,451,456 | B2 | 5/2013 | Babayoff |
| 9,307,165 | B2* | 4/2016 | Levy ................... G06K 9/20 |
| 9,724,177 | B2 | 8/2017 | Levin |
| 9,987,108 | B2 | 6/2018 | Levin et al. |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer |
| 2004/0128010 | A1 | 7/2004 | Pavlovskaia et al. |
| 2005/0055118 | A1 | 3/2005 | Nikolskiy et al. |
| 2006/0212260 | A1 | 9/2006 | Kopelman et al. |
| 2010/0061612 | A1* | 3/2010 | Reisman ............ G06T 3/0081 382/131 |
| 2010/0283781 | A1 | 11/2010 | Kriveshko et al. |
| 2011/0050848 | A1* | 3/2011 | Rohaly ............... G06T 15/10 348/43 |
| 2012/0062557 | A1* | 3/2012 | Dillon ................ A61C 7/002 345/419 |
| 2012/0300020 | A1 | 11/2012 | Arth et al. |
| 2016/0064898 | A1* | 3/2016 | Atiya ............ G02B 27/0905 356/601 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 2428764 A1 | 3/2012 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-2014027025 A1 | 2/2014 |
| WO | WO-2014139079 A1 | 9/2014 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237- 253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy. swin.edu.au/—pbourke/prolection/coords>.

Boyd et al., "Three Dimensional Diagnosis and Orthodontic Treatment of Complex Malocclusions With the lnvisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

(56) References Cited

OTHER PUBLICATIONS

Burstone (interview), "Dr. Charles J. Burstone on The Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, "Part 3 The Computer Gives New Vision—Literally, Part 4 Bytes 'N Bites—The Computer Moves from the Front Desk to the Operatory," Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet< http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates In Orthodontics and Orthognathic Surgery," JCO, pp. 262-328 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstresspu-tonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances—Pro Lab, 1 page 1998).
International search report and written opinion dated Nov. 13, 2015 for PCT/IB2015/001403.
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports On Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.

(56) References Cited

OTHER PUBLICATIONS

Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue ... The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue ... The Simple, Affordable, No-Braces Treatment, Allesee HJ Orthodontic Appliances—Pro Lab product information for patients,< http://ormco.com/aoa/appliancesservices/RWB/patients.html>, 2 pages (May 19, 2003).
The Choice Is Clear: Red, White & Blue ... The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
TRU-TAIN Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.

(56) References Cited

OTHER PUBLICATIONS

U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be A Candidate For This Invisible No-Braces Treatment, Allesee Orthodontic Appliances—Pro Lab product information for patients, 2 pages (2002).

* cited by examiner

VIEWFINDER WITH REAL-TIME TRACKING FOR INTRAORAL SCANNING

CROSS-REFERENCE

This application is a continuation application of U.S. application Ser. No. 15/645,243, filed Jul. 10, 2017, now U.S. Pat. No. 9,987,108, issued Jun. 5, 2018, which is a continuation application of U.S. application Ser. No. 14/463,464, filed Aug. 19, 2014, now U.S. Pat. No. 9,724,177, issued Aug. 8, 2017, which is incorporated herein by reference in its entirety and to which application we claim priority under 35 USC § 120.

BACKGROUND OF THE INVENTION

Many dental and orthodontic procedures require accurate three-dimensional (3D) topographical measurements of a patient's intraoral cavity. For example, in the design and fabrication of dental prostheses (e.g., crowns or bridges), 3D models of the prosthesis site and surrounding dentition are typically used to ensure proper fit of the prosthesis. In many orthodontic procedures, 3D models of the patient's dental arches are utilized to design orthodontic appliances and develop treatment plans (e.g., to correct malocclusions). Various approaches can be used to produce such 3D models. For example, a physical model can be constructed from an impression of the patient's dentition. Alternatively, the intraoral cavity can be scanned to provide a virtual model suitable for use within computer-assisted design and computer-assisted manufacture (CAD/CAM) methods as well as digital treatment planning.

Scanning of the intraoral cavity may be performed by a dental or orthodontic practitioner. Previous methods and systems for scanning the intraoral cavity, however, can be less than ideal with regards to providing guidance to the dental or orthodontic practitioner during the scanning procedure. As a result, incomplete scanning coverage or insufficient overlap between scans may reduce the accuracy of the subsequent digital model. Conversely, excessive overlap between scans can be inefficient and unnecessarily lengthen the duration of the scanning procedure.

Thus, there is a need for improved methods and systems for scanning an intraoral cavity of a patient.

SUMMARY

Embodiments provide improved methods and systems for scanning an intraoral cavity of a patient. In many embodiments, methods and systems for scanning an intraoral cavity comprise displaying a viewfinder image corresponding to a field of view of an intraoral scanner and one or more indicators depicting previously scanned portions of the intraoral cavity. The scanning methods and systems described herein can provide real-time visual guidance of scanning coverage of the intraoral cavity, thereby providing faster and more efficient intraoral scanning. In many embodiments, an optical axis of the scanner is aligned with an optical axis of the viewfinder in order to determine the scanned portions of the intraoral cavity directly from the viewfinder images. Determining the scanned portions of the intraoral cavity from the viewfinder images can provide faster scanning and improve real-time display of the scanned portions of the intraoral cavity with the real-time images shown to the user, which can facilitate alignment of the scanner with the intraoral cavity.

In a first aspect, a method for scanning an intraoral cavity of a patient comprises capturing one or more viewfinder images of one or more portions of the intraoral cavity of the patient, each of said one or more viewfinder images corresponding to a field of view of an intraoral scanner, and scanning the one or more portions of the intraoral cavity with the intraoral scanner to generate one or more topography scans of the one or more portions of the intraoral cavity. The one or more topography scans may correspond to the one or more viewfinder images. The method may further comprise capturing a viewfinder image of a portion of the intraoral cavity, the viewfinder image overlapping with the one or more viewfinder images. An area of overlap of the viewfinder image with the one or more viewfinder images can be determined. One or more indicators of the area of overlap can be displayed on one or more locations of a display in order to provide guidance for positioning the field of view of the intraoral scanner.

In another aspect, a system for scanning an intraoral cavity of a patient comprises an intraoral scanner, a viewfinder, a display, and a processing unit. The intraoral scanner can comprise an optical assembly configured to focus light onto one or more portions of the intraoral cavity in order to generate one or more topography scans of the one or more portions. The viewfinder can be optically aligned with the intraoral scanner in order to capture one or more viewfinder images corresponding to the field of view of the intraoral scanner. The display can be configured to display one or more indicators on one or more locations in order to provide guidance for positioning the field of view of the intraoral scanner. The processing unit can be operatively coupled to the intraoral scanner, the display, and the viewfinder. The processing unit can comprise instructions to determine an area of overlap between the viewfinder image captured by the viewfinder and one or more viewfinder images captured by the viewfinder. The one or more viewfinder images can correspond to the one or more topography scans generated by the intraoral scanner. The processing unit can comprise instructions to show the area of overlap of the viewfinder image and the one or more viewfinder images on the display.

Other benefits and features of embodiments the present invention will be apparent in view of the specification, claims, and appended figures.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
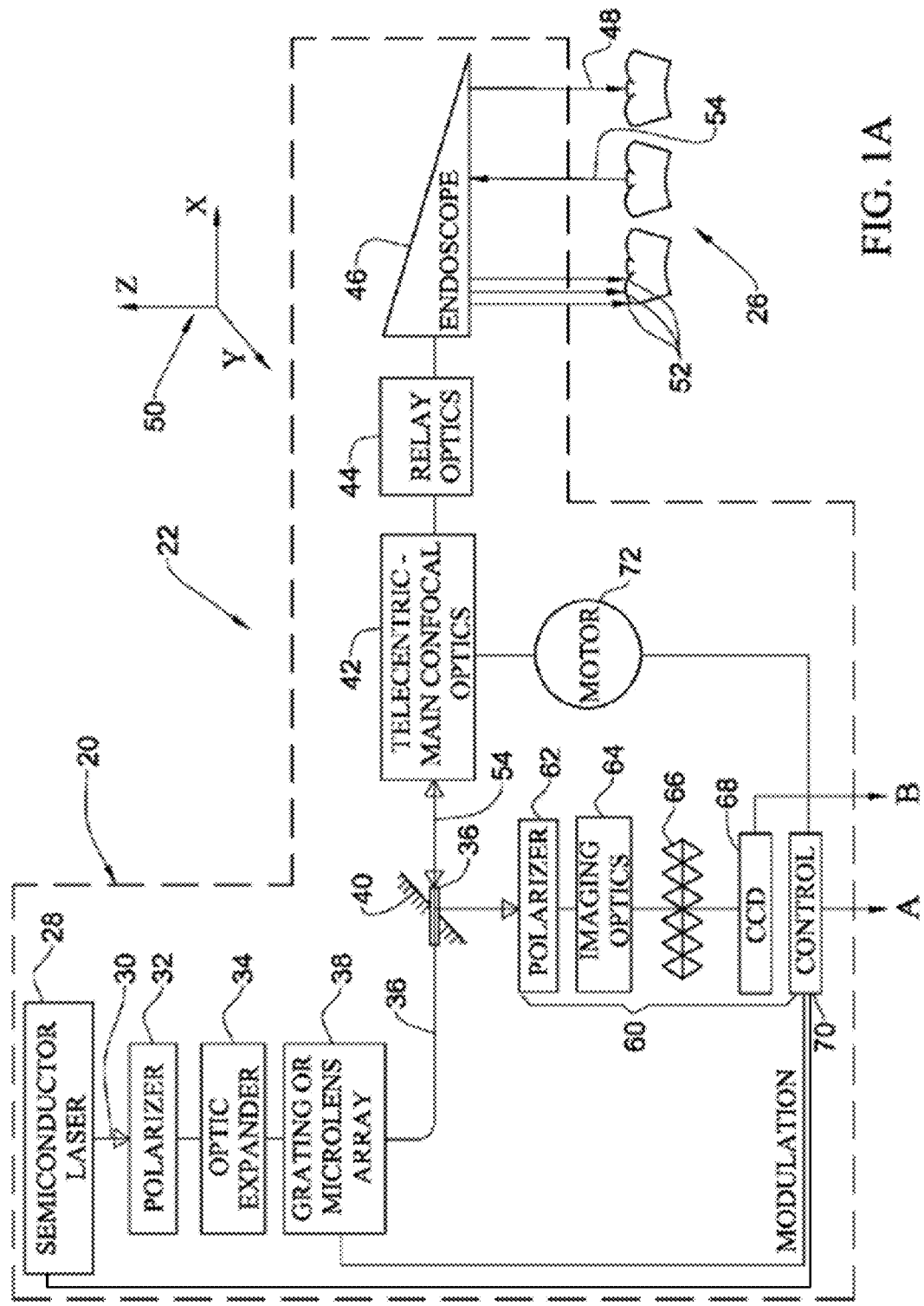
FIGS. 1A and 1B schematically illustrate, by way of a block diagram, an apparatus in accordance with many embodiments (FIG. 1B is a continuation of FIG. 1A)

Methods and systems described herein provide visual guidance for a user (e.g., a dental or orthodontic practitioner) during an intraoral scanning procedure. The method and systems described herein can be combined in many ways and are well suited for combination for intraoral scanners used for measuring portions of the intraoral cavity, for example. Any of the embodiments provided herein can be combined with other embodiments to the extent that such embodiments are not inconsistent with the teachings described herein.

As used herein A and/or B encompasses A alone, B alone, and combinations of A and B.

In many embodiments, one or more indicators depicting previously scanned portions of the intraoral cavity are displayed as an overlay on a viewfinder image depicting the field of view of an intraoral scanner. The one or more indicators can be updated as the scanner is moved, such that the user receives real-time visual guidance of scanning coverage and progress during the scanning procedure. Based on the displayed indicators, the practitioner can adjust the position of the scanner within the intraoral cavity to control the amount of overlap between the scans and ensure satisfactory scanning coverage of the region of interest. The embodiments provided herein can be used to improve the efficiency and ease of use of intraoral scanning systems.

In one aspect, a method is provided for scanning an intraoral cavity of a patient. In many embodiments, the method comprises capturing one or more viewfinder images of one or more portions of the intraoral cavity of the patient, each of said one or more viewfinder images corresponding to a field of view of an intraoral scanner, and scanning the one or more portions of the intraoral cavity with an intraoral scanner to generate one or more topography scans of the one or more portions of the intraoral cavity. The one or more topography scans may correspond to the one or more viewfinder images. The method further comprises capturing a viewfinder image of a portion of the intraoral cavity, the viewfinder image overlapping with the one or more viewfinder images. An area of overlap of the viewfinder image with the one or more viewfinder images can be determined. One or more indicators of the area of overlap can be displayed on one or more locations of a display in order to provide guidance for positioning the field of view of the intraoral scanner.

In many embodiments, the display and one or more indicators provide visual guidance representing the area of overlap on a viewfinder image. For example, the one or more indicators may mark one or more boundary locations of the area of overlap or may identify a boundary of the area of overlap. The one or more indicators on the one or more locations of the display may move on the display when a user adjusts the portion of the intraoral cavity within the field of view of the intraoral scanner in order to allow the user to position the field of view of the intraoral scanner. The method may further comprise scanning the portion of the intraoral cavity with the one or more indicators displayed at the one or more locations on the display. Subsequent viewfinder images can be shown with the one or more indicators shown at the one or more locations on the display. Optionally, the one or more viewfinder images can comprise a warning indicator if the area of overlap is smaller than a predetermined amount.

The area of overlap can be determined using any suitable technique. In many embodiments, the one or more viewfinder images are compared to the viewfinder image in order to determine the area of overlap of the viewfinder image with the one or more viewfinder images corresponding to the one or more topography scans. Determining the area of overlap may comprise registering the viewfinder image to the one or more viewfinder images. For example, registering the viewfinder image to the one or more viewfinder images can comprise identifying one or more features present in both the viewfinder image and the one or more viewfinder images. Registering the viewfinder image to the one or more viewfinder images can comprise at least one of transforming or deforming the viewfinder image to increase it similarity to the one or more viewfinder images.

Following the determination and display of the one or more indicators, intraoral topography scans can be generated using the indicators as a visual guide for aiming the scanner. In many embodiments, the method further comprises positioning the intraoral scanner within the intraoral cavity guided at least in part by the one or more indicators. A portion of the intraoral scanner can be scanned to obtain a topography scan thereof. The method may further comprise recording a viewfinder image corresponding to the topography scan while scanning the portion of the intraoral cavity with the intraoral scanner. The one or more viewfinder images can be updated to include the recorded viewfinder image.

In another aspect, a system is provided for scanning an intraoral cavity of a patient. In many embodiments, the system comprises an intraoral scanner, a viewfinder, a display, and a processing unit. The intraoral scanner can comprise an optical assembly configured to focus light onto one or more portions of the intraoral cavity in order to generate one or more topography scans of the one or more portions. The viewfinder can be optically aligned with the intraoral scanner in order to capture one or more viewfinder images corresponding to the field of view of the intraoral scanner. The display can be configured to display one or more indicators on one or more locations in order to provide guidance for positioning the field of view of the intraoral scanner. The processing unit can be operatively coupled to the intraoral scanner, the display, and the viewfinder. The processing unit can comprise instructions to determine an area of overlap between the viewfinder image captured by the viewfinder and one or more viewfinder images captured by the viewfinder. The one or more viewfinder images can correspond to the one or more topography scans generated by the intraoral scanner. The processing unit can comprise instructions to show the area of overlap of the viewfinder image and the one or more viewfinder images on the display.

The design of the intraoral scanner can be varied as desired. In many embodiments, the intraoral scanner configured for point-and-shoot scanning. Alternatively, the intraoral scanner can be configured for continuous scanning.

Various approaches can be used to determine the area of overlap. In many embodiments, the processing unit comprises instructions to determine the area of overlap by registering the viewfinder image to the one or more viewfinder images. Registering the viewfinder image to the one or more viewfinder images can comprise identifying one or more features present in the viewfinder image and the one or more viewfinder images. Registering the viewfinder image to the one or more viewfinder images can comprise at least one of transforming or deforming the viewfinder image to increase its similarity to the one or more viewfinder images.

The indicators can include any graphical element suitable for representing the area of overlap. In many embodiments, the one or more indicators comprise a boundary of the area of overlap or a coloring of the area of overlap. The one or more indicators can comprise a warning indicator if the area of overlap is smaller than a predetermined amount.

In many embodiments, the processing unit comprises instructions to record the viewfinder image while the intraoral scanner is scanning the intraoral cavity and add the recorded viewfinder image to the one or more viewfinder images.

In many embodiments, the display unit is configured to display surface topography data of the one or more portions of the intraoral cavity.

Figure 1B:
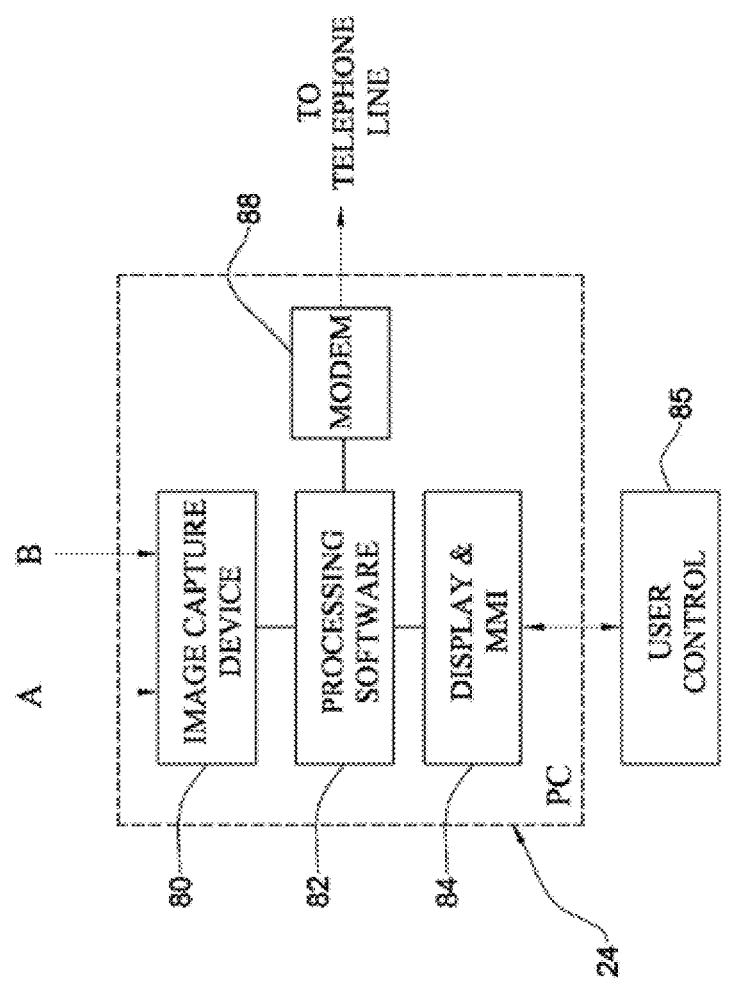

Turning now to the drawings, in which like numbers and/or words designate like elements in the various figures, FIGS. 1A and 1B illustrate an apparatus 20 for measuring surface topography optically. The apparatus 20 includes an optical device 22 coupled to a processor 24. The embodiment illustrated in FIGS. 1A and 1B is particularly useful for measuring surface topography of a patient's teeth 26. For example, the apparatus 20 can be used to measure surface topography of a portion of the patient's teeth where at least one tooth or portion of tooth is missing to generate surface topography data for subsequent use in design and/or manufacture of a prosthesis for the patient (e.g., a crown or a bridge). It should be noted, however, that the invention is not limited to measuring surface topography of teeth, and applies, mutatis mutandis, also to a variety of other applications of imaging of three-dimensional structure of objects (e.g., for the recordal of archeological objects, for imaging of a three-dimensional structure of any suitable item such as a biological tissue, etc.).

The optical device 22 includes, in the illustrated embodiment, a light source 28 such as a semiconductor laser unit emitting a laser light, as represented by arrow 30. The light passes through a polarizer 32, which causes the light passing through the polarizer 32 to have a certain polarization. The light then enters into an optic expander 34, which increases the diameter of the light beam 30. The light beam 30 then passes through a module 38, which can, for example, be a grating or a micro lens array that splits the parent beam 30 into a plurality of light beams 36, represented here, for ease of illustration, by a single line.

The optical device 22 further includes a partially transparent mirror 40 having a small central aperture. The mirror 40 allows transfer of light from the laser unit 28 through the downstream optics, but reflects light travelling in the opposite direction. It should be noted that in principle, rather than a partially transparent mirror, other optical components with a similar function may be used (e.g., a beam splitter). The aperture in the mirror 40 improves the measurement accuracy of the apparatus. As a result of this mirror structure, the light beams produce a light annulus on the illuminated area of the imaged object as long as the area is not in focus. The annulus becomes a sharply-focused illuminated spot when the light beam is in focus relative to the imaged object. Accordingly, a difference between the measured intensity when out-of-focus and in-focus is larger. Another advantage of a mirror of this kind, as opposed to a beam splitter, is that internal reflections that occur in a beam splitter are avoided, and hence the signal-to-noise ratio is greater.

The optical device 22 further includes confocal optics 42, typically operating in a telecentric mode, relay optics 44, and an endoscopic probe member 46. In many embodiments, the confocal optics 42 is configured to avoid distance-introduced magnification changes and maintain the same magnification of the image over a wide range of distances in the Z direction (the Z direction being the direction of beam propagation). In many embodiments, the relay optics 44 is configured to maintain a certain numerical aperture of the light beam's propagation.

The endoscopic probe member 46 can include a light-transmitting medium, which can be a hollow object defining within it a light transmission path or an object made of a light transmitting material (e.g., a glass body or tube). The light-transmitting medium may be rigid or flexible (e.g., fiber optics). In many embodiments, the endoscopic probe member 46 includes a mirror 95 of the kind ensuring a total internal reflection and directing the incident light beams towards the patient's teeth 26. The endoscope 46 thus emits a plurality of incident light beams 48 impinging on to the surface of the patient's teeth 26.

In many embodiments, the distance between the endoscopic probe member 46 and the patient's teeth 26 is determined by measuring one or more characteristics of returning light beams 54 generated by illuminating the teeth 26 with the incident light beams 48. Such characteristics can include, for example, intensity, wavelength, polarization, phase shift, interference, and/or dispersion of the returning light beams 54. Any description herein relating to light intensity can also be applied to other suitable characteristics of light, and vice-versa. The measurements of the characteristic(s) can be used to detect whether the incident light beams 46 are focused on the surface of the teeth 26 and thereby determine the distance between the endoscopic probe member 46 and the teeth 26.

For example, as depicted in FIGS. 1A and 1B, the distance can be determined based on measured light intensities. The incident light beams 48 form an array of light beams arranged in an X-Y plane, relative to a Cartesian reference frame 50, and propagating along the Z axis. When the incident light beams 48 are incident upon an uneven surface, resulting illuminated spots 52 are displaced from one another along the Z axis, at different $(X_i, Y_i)$ locations. Thus, while an illuminated spot 52 at one location may be in focus for a given focal length produced by the confocal optics 42, illuminated spots 52 at other locations may be out-of-focus. Therefore, the light intensity of the returned light beams of the focused spots will be at its peak, while the light intensity at other spots will be off peak. Thus, for each illuminated spot, a plurality of measurements of light intensity are made at different positions along the Z-axis and for each of such $(X_i, Y_i)$ locations, typically the derivative of the intensity over distance (Z) will be made, and the $Z_i$ yielding maximum derivative, $Z_0$, will be the in-focus distance. As pointed out above, where, as a result of use of the mirror with aperture 40, the incident light forms a light disk on the surface when out of focus and a sharply-focused light spot only when in focus, the distance derivative will be larger when approaching in-focus position thus increasing accuracy of the measurement.

The light reflected from each of the illuminated spots 52 includes a beam travelling initially in the Z axis in the opposite direction of the optical path traveled by the incident light beams. Each returned light beam 54 corresponds to one of the incident light beams 36. Given the unsymmetrical properties of mirror 40, the returned light beams 54 are reflected in the direction of a detection assembly 60. The detection assembly 60 includes a polarizer 62 that has a plane of preferred polarization oriented normal to the polarization plane of polarizer 32. The returned polarized light beam 54 pass through an imaging optics 64, typically a lens or a plurality of lenses, and then optionally through an array of pinholes 66. Each returned light beam 54 may pass at least partially through a respective pinhole of the array of pinholes 66. A charge-coupled device (CCD) sensor array 68 includes a matrix of sensing elements. In many embodiments, each sensing element represents a pixel of the image and each sensing element corresponds to one pinhole in the array 66.

The sensor array 68 is connected to an image-capturing module 80 of the processor unit 24. The light intensity measured by each of the sensing elements of the sensor array 68 is analyzed, in a manner described below, by the processor 24.

The optical device 22 includes a control module 70 that controls operation of the light source 28. The control module 70 can be used in conjunction with any suitable mechanism or configuration for controlling the focal positions of the incident light beams 36. For example, in many embodiments, a motor 72 is drivingly coupled with the confocal optics 42 so as to scan the focus of the light beams through a range of focal depths along the Z axis. In a single sequence of operation, the control unit 70 induces motor 72 to reconfigure the confocal optics 42 to change the focal plane location and then, after receipt of a feedback that the location has changed, the control module 70 induces the laser 28 to generate a light pulse. The control module 70 synchronizes the operation of the image-capturing module 80 with the operation of the confocal optics 42 and the light source 28 during acquisition of data representative of the light intensity from each of the sensing elements. Then, in subsequent sequences, the confocal optics 42 causes the focal plane to change in the same manner and intensity data acquisition continues over a range of focal lengths.

The intensity data is processed by the processor 24 per processing software 82 to determine relative intensity in each pixel over the entire range of focal planes of confocal optics 42. As explained above, once a certain light spot is in focus on the three-dimensional structure being measured, the measured intensity of the returning light beam will be maximal. Thus, by determining the $Z_i$ corresponding to the maximal light intensity or by determining the minimum derivative of the light intensity, for each pixel, the relative in-focus focal length along the Z axis can be determined for each light beam. Thus, data representative of the three-dimensional topography of the external surfaces of the teeth is obtained. A resulting three-dimensional representation can be displayed on a display 84 and manipulated for viewing (e.g., viewing from different angles, zooming-in or out) by a user control module 85 (e.g., a computer keyboard). In addition, the data representative of the surface topology can be transmitted through an appropriate data port such as, for example, a modem 88 or any suitable communication network (e.g., a telephone network) to a recipient (e.g., to an off-site CAD/CAM apparatus).

By capturing, in this manner, relative distance data between the probe and the structure being measured from two or more angular locations around the structure (e.g., in the case of a teeth segment, from the buccal direction, lingual direction and/or optionally from above the teeth), an accurate three-dimensional representation of the structure can be generated. The three-dimensional data and/or the resulting three-dimensional representation can be used to create a virtual model of the three-dimensional structure in a computerized environment and/or a physical model fabricated in any suitable fashion (e.g., via a computer controlled milling machine, a rapid prototyping apparatus such as a stereolithography apparatus).

As already pointed out above, a particular and preferred application is imaging of a segment of teeth having at least one missing tooth or a portion of a tooth. The resulting three-dimensional surface topography data can, for example, be used for the design and subsequent manufacture of a crown or any other prosthesis to be fitted into this segment.

Figure 2A:
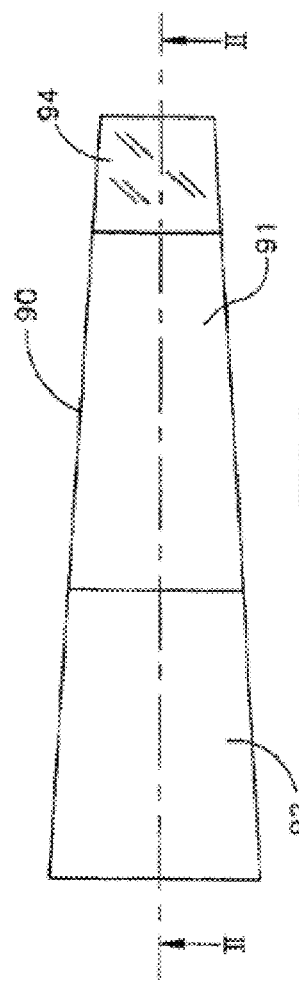
FIG. 2A illustrates a top view of a probing member in accordance with many embodiments.
Figure 2B:
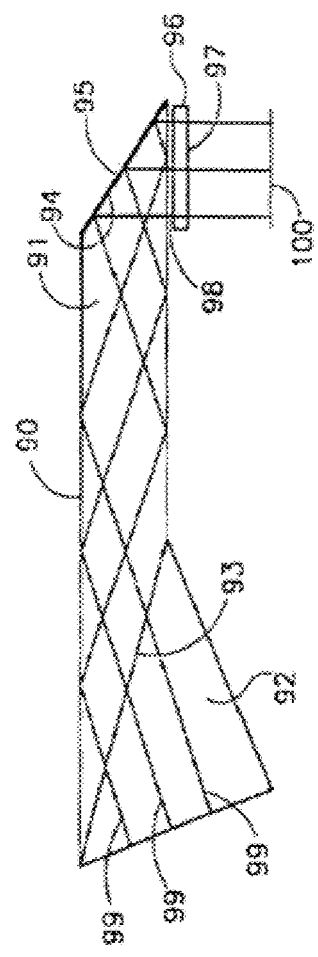
FIG. 2B illustrates a longitudinal cross-section through the probing member of FIG. 2A, depicting exemplary rays passing therethrough.

Referring now to FIGS. 2A and 2B, a probing member 90 is illustrated in accordance with many embodiments. The probing member 90 can be made of a light transmissive material (e.g., glass, crystal, plastic, etc.) and includes a distal segment 91 and a proximal segment 92, tightly glued together in an optically transmissive manner at 93. A slanted face 94 is covered by a reflective mirror layer 95. A transparent disk 96 (e.g., made of glass, crystal, plastic, or any other transparent defining a sensing surface 97 is disposed along the optical path distal to the mirror layer 95 so as to leave an air gap 98 between the glass disk 96 and the distal segment 91. The transparent disk 96 is fixed in position by a holding structure (not shown). Three light rays 99 are represented schematically. As can be seen, the light rays 99 reflect from the walls of the probing member 90 at an angle in which the walls are totally reflective, reflect from the mirror layer 95, and then propagate through the sensing face 97. The light rays 99 are focused on a focusing plane 100, the position of which can be changed by the confocal optics 42.

Figure 3:
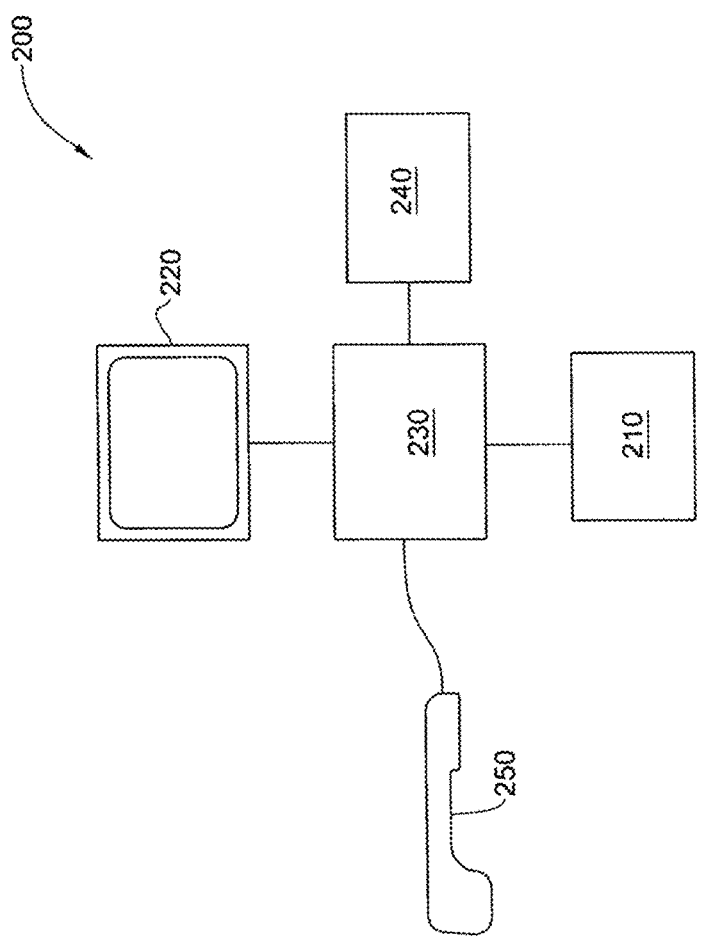
FIG. 3 illustrates a system for scanning an intraoral cavity, in accordance with many embodiments.

FIG. 3 illustrates the main elements of a system 200 for scanning an intraoral cavity, in accordance with many embodiments. The system 200 includes an input unit 210 (e.g., a keyboard, mouse, joystick, tablet, or touch screen), a display or output module 220 (e.g. a screen, monitor, or printer), a processing unit 230 (e.g., comprising one or more processors such as a CPU), and a memory 240. A handheld scanner 250 (e.g., an intraoral scanner) is operatively connected to the system 200. Any suitable scanning system or device for obtaining 3D topographical data of the intraoral cavity can be used for the scanner 250, such as the optical device 22. For example, the scanner 250 can be a "point-and-shoot" scanner configured such that each scan event is initiated by a specific user input command (e.g., a button press, mouse click, etc). In such embodiments, each scan can be performed while the scanner 250 is held stationary at a desired position and orientation. As another example, the scanner 250 can be a "continuous scanner" configured to continuously obtain scan data without requiring user input to specifically initiate each scan (e.g., based on control signals produced by the processing unit 230). In such embodiments, scanning can be performed continuously or at predetermined time intervals as the scanner 250 moves through a plurality of positions and orientations relative to the intraoral cavity. Scan data collected by the scanner 250 can be processed by the processing unit 230 to reconstruct the surface topography of the intraoral cavity, thereby generating a 3D digital model of the intraoral cavity. The surface topography data can be presented to the user (e.g., as a 3D graphical representation on the display 220) and/or stored for subsequent applications (e.g., in the memory 240).

In many embodiments, the intraoral scanning systems provided herein include a viewfinder that provides two-dimensional image data of the intraoral cavity corresponding to the field of view of the scanner. In many embodiments, the viewfinder and scanner are optically aligned such that the field of view of the viewfinder is the same or similar to the field of view of the scanner. The viewfinder images can be displayed to a user in order to guide the scanning procedure and can be updated as the scanner moves to reflect changes in the scanner's field of view. Accordingly, the user can adjust the position and orientation of the scanner based on the displayed viewfinder images in order to ensure satisfactory scanning coverage of the targeted portion of the intraoral cavity.

The approaches provided herein can be used with any suitable scanner and viewfinder system. The viewfinder can include any suitable imaging device operable to provide images corresponding to the field of view of the scanner, such as a camera suitable for capturing monochromatic or color image data. For example, the viewfinder images may represent the field of view of the scanner, e.g., in terms of viewing angle, coverage area, etc. The viewfinder field of view may be similar to or larger than the scanner field of view, such that the viewfinder images represent the entirety of the field of view of the scanner. Alternatively, the viewfinder field of view may be smaller than or partially overlapping with the scanner field of view, such that the viewfinder images represent a subset of the field of view of the scanner. In many embodiments, the viewfinder is adapted to record image data in real time, such that the viewfinder images are continuously displayed and updated as the scanner is moved. For example, the viewfinder can include a camera with a suitable video capture rate for real-time display. Alternatively, the viewfinder can record image data at a video capture rate different than the video display rate.

Figure 4:
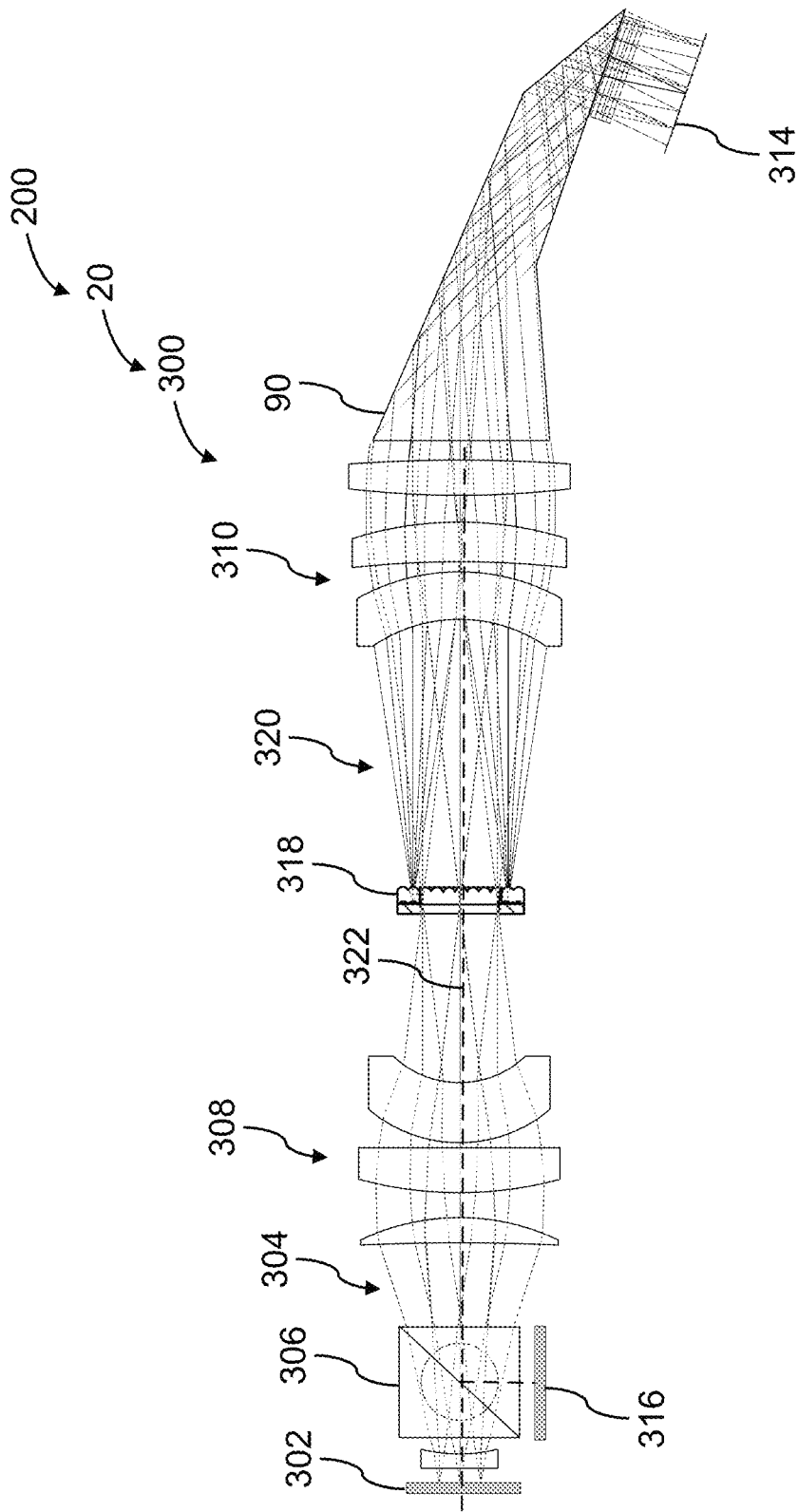
FIG. 4 illustrates an optical system with aligned scanner and viewfinder optics, in accordance with many embodiments.

FIG. 4 illustrates an optical system 300 with aligned scanner and viewfinder optics, in accordance with many embodiments. At least some of the elements of the optical system 300 can be combined with the other systems and devices described herein. For example, the optical system 300 can be incorporated within the apparatus 20, which may be part of the scanning system 200. In many embodiments, at least some of the components of the optical system 300 form part of an intraoral scanning device, such as the handheld scanner 250. In the system 300, the components of the scanner and viewfinder are integrated into a single device, such at least some portions of the optical path of the scanner overlap with the optical path of the viewfinder and at least some optical components of the system 300 are shared between the scanner and viewfinder. The system 300 comprises a scanner illumination unit 302 that produces a two-dimensional array of light beams 304 (e.g., an array of laser beams) for surface topography scanning. The array of light beams 304 can propagate through a polarizing beam splitter 306, a first set of lens elements 308, a second set of lens elements 310, and a probing member 90 so as to illuminate the surface of a targeted object with a two-dimensional array of light spots. In many embodiments, the array of light beams 304 is focused to a focal plane 314 external to the probing member 90. Light beams reflected from the surface can pass back through the probing member 90 and lens elements 308, 310 and are directed by the beam splitter 306 onto an detector unit 316 (e.g., sensor array 68). The detector unit 316 can include a plurality of sensor elements used to measure characteristics of the returning light (e.g., light intensity) in order to determine the surface topography, as previously described herein.

The system 300 also includes a viewfinder illumination unit 318 that provides a plurality of light beams 320 for generating viewfinder image data. For example, the viewfinder illumination unit 318 can include a plurality of LEDs. The LEDs can be arranged in a ring configuration, with the central aperture of the ring sized to permit light beams of the array 304 and returning light beams from the object surface to pass through. The light beams 320 produced by the viewfinder illumination unit 318 can propagate through the second set of lens elements 310 and the probing member 90 to illuminate the object surface. Light reflected from the surface can pass back through the optics and onto the sensor elements of the detector unit 316, as described above. The sensor data can subsequently be processed using techniques known to those of skill in the art to provide viewfinder images. In many embodiments, the scanner and viewfinder optics are optically aligned so as to share a common optical axis 322, such that the field of view of the scanner is the same or similar to the field of view of the viewfinder and the viewfinder images provided by the viewfinder correspond to the field of view of the scanner.

In many embodiments, the system 300 can utilize a single detector unit 316 to generate scan data and viewfinder image data, rather than having separate detector units for topography scanning and image capture. Alternatively, the system 300 may comprise separate detectors for generating scanning data from the array of light beams 304 and for generating viewfinder image data, in which the scanner and viewfinder optical axes are optically aligned, for example.

The viewfinder illumination unit 318 can be adapted to provide monochromatic or polychromatic illumination (e.g., via colored LEDs). In many embodiments, the illumination unit 318 sequentially illuminates the targeted object with different wavelengths (e.g., red, green, and blue wavelengths) and the detector unit 316 obtains a monochromatic image corresponding to each wavelength. The different monochromatic images can be subsequently be processed and merged to provide a composite color image of the object. Optionally, the system 300 can include chromatic dispersion optics along the optical path between the illumination unit 318 and the imaged object, such that each wavelength of light is focused to a different focal depth. Accordingly, the focused and unfocused areas of each monochromatic image may differ based on the particular illumination wavelength used. Suitable image processing algorithms can be used to identify the focused areas of each image in order to increase the clarity and precision of the final composite image.

An intraoral scanning procedure may involve capturing topographical scan data of multiple portions of the patient's intraoral cavity. As previously described, the user can view the image data provided by the viewfinder (e.g., via a graphical interface provided on a display, as described in further detail herein) in order to determine which portions of the intraoral cavity are included in the current field of view of the scanner. Furthermore, suitable guidance mechanisms can be implemented to indicate to the user which portions of the cavity have already been scanned in order to improve scanning efficiency and reduce unnecessary rescanning. These guidance mechanisms can include visual indicators provided on a display (e.g., as an overlay on top of the current viewfinder image) that permit the user to rapidly and accurately assess whether the current field of view is situated at an appropriate location relative to the areas of previous scan coverage. The user can then position and orient the field of view of the scanner accordingly so as to scan targeted portions of the intraoral cavity while reducing the overlap with previously scanned areas. In many embodiments, the visual indicators can be updated or adjusted according to the scanning progress and scanner movement, thereby providing real-time or near real-time scanning guidance.

Figure 5A:
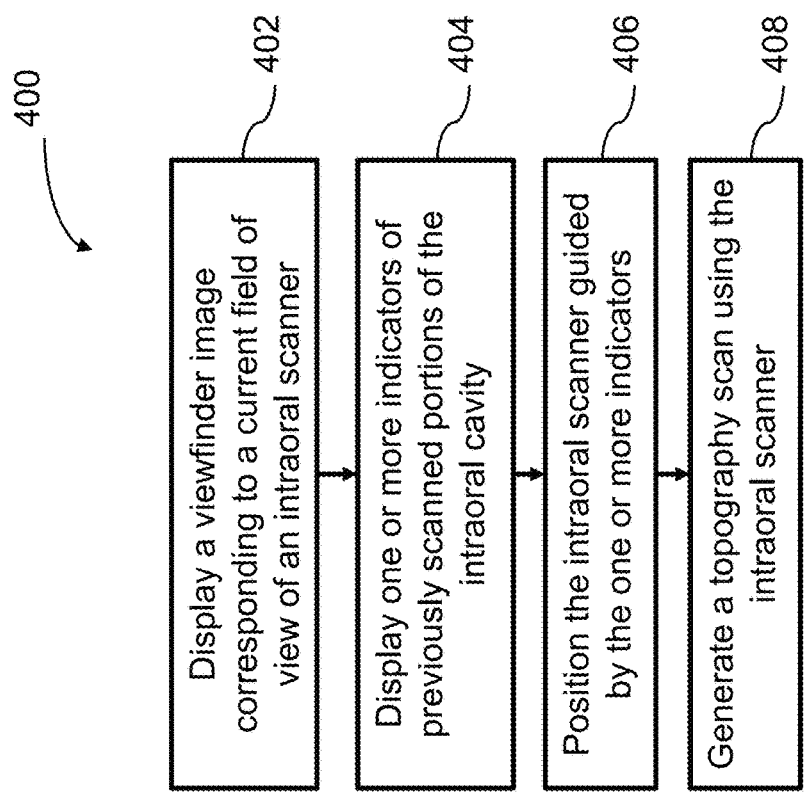
FIG. 5A illustrates a method for guiding scanning of an intraoral cavity of a patient, in accordance with many embodiments.

FIG. 5A illustrates a method 400 for guiding scanning of an intraoral cavity of a patient, in accordance with many embodiments. As with all methods presented herein, any embodiment of the systems and devices described herein can be used to practice the method 400 and at least some of the steps of the method 400 can be performed by one or more processors of a controller or other computing system.

In step 402, a viewfinder image corresponding to a current field of view of an intraoral scanner is displayed (e.g., on the display 220). As described herein, the viewfinder image may comprise video image data captured by a suitable imaging device such as a camera. The displayed viewfinder images can be updated at a suitable rate (e.g., approximately 30 Hz) so as to provide real-time or approximately real-time updates of the field of view as the scanner is moved relative to the intraoral cavity. In embodiments where the extent of the viewfinder image differs from the extent of the scanner field of view, one or more markers can be displayed on the viewfinder image in order to allow the user to identify the portions of the viewfinder image that overlap with the scanner field of view. For example, graphical elements such as symbols, shapes, coloring, textures, etc. can be overlaid onto the viewfinder image in order to delineate the spatial relationship of the field of view of the scanner relative to the displayed viewfinder image.

In step 404, one or more indicators of previously scanned portions of the intraoral cavity are displayed (e.g., on the display 220). Exemplary methods for determining the extent of previously scanned portions and generating corresponding indicators are described in greater detail below. The one or more indicators can comprise suitable graphical elements (e.g., symbols, shapes, text, coloring, textures, instructions, animations) positioned at one or more locations on the display so as to provide visual guidance to a user (e.g., dental practitioner) indicating which portions of the cavity have been already been scanned. For example, the indicators can comprise lines, borders, shading, coloring, etc. displayed at one or more locations so as to identify a boundary of the area of overlap. The indicators at the one or more locations can be used to mark one or more boundary locations of the area of overlap. In many embodiments, the one or more indicators are overlaid onto the displayed viewfinder image, thereby indicating the extent of the previously scanned portions relative to the current field of view of the scanner. Optionally, the one or more indicators may be overlaid onto viewfinder images subsequent to the image of step 402, e.g., in embodiments where the viewfinder video rate differs from the indicator update rate, as described in further detail below.

Furthermore, the indicators can also be used to warn the user of potential problems, such as insufficient overlap with previous scans that would result in gaps in scanning coverage, or excessive overlap with previous scans that would reduce scanning efficiency. For example, a warning indicator can be displayed if the amount of overlap is smaller than a predetermined amount. In some instances, the warning indicator can be displayed if the amount of overlap is zero. The predetermined amount can be based on user input and/or a property of the scanning system. For example, the predetermined amount can be based on the minimum amount of overlap between scans needed for the scanning system to properly reconstruct the scanned topography. Alternatively or in combination, the warning indicator can be displayed if the amount of overlap is greater than a predetermined amount. For example, the warning indicator can be used to alert the user that sufficient scan data for the corresponding portion of the intraoral cavity has already been obtained. The warning indicator can be any suitable indicator including or more of text, numbers, symbols, lines, shapes, coloring, shading, or blurring, as previously described. Optionally, the warning indicator can comprise an audible warning, such as a sound, tone, or spoken alert.

In step 406, the intraoral scanner is positioned, the positioning being guided at least in part by the one or more indicators. The viewfinder image and/or indicators can be updated in real-time or approximately real-time as the scanner is moved. For instance, as the user moves the scanner to adjust the portion of the intraoral cavity within the field of view of the scanner, the indicators can move correspondingly to correctly depict the previously scanned portions relative to the intraoral cavity portion. Accordingly, the user can reposition the field of view of the scanner within the intraoral cavity, for example, to adjust the amount of overlap between scans, verify the extent of scan coverage, and/or identify unscanned regions. For example, in response to a warning indicator alerting the user to insufficient overlap, the user can maneuver the scanner to increase the area of overlap between the current viewfinder image and the previously scanned portion of the intraoral cavity.

In step 408, a topography scan of a portion of the intraoral cavity is generated using the intraoral scanner, in accordance with the embodiments presented herein. The topography scan can be performed while the one or more indicators are being shown (e.g., at one or more locations on the display).

In many embodiments, the method 400 can be repeated throughout the duration of a scanning procedure in order to provide the user with real-time tracking of scanning progress. The displayed indicators can be updated with each topography scan so as to reflect the current extent of scanning coverage. Additionally, the locations of the displayed indicators on the display can be adjusted as the current viewfinder image changes (e.g., based on changes to the position and/or orientation of the intraoral scanner) so that the user can ascertain the degree to which the current field of view overlaps with previous scan data.

The scanning guidance mechanisms provided herein can utilize various approaches in order to determine and display the extent of previous scan coverage relative to a current viewfinder image. In many embodiments, areas of previous scan coverage within a current viewfinder image are identified based on previously obtained viewfinder images. For example, the viewfinder can be configured to capture and store viewfinder images corresponding to the topography scans generated by the scanner. Each recorded viewfinder image can provide a representation of the portion of the intraoral cavity covered by the corresponding topography scan. The recorded viewfinder images can be compared to a current viewfinder image depicting the current field of view of the scanner in order to identify scanned and unscanned areas, e.g., by determining the area of overlap between the current viewfinder images and recorded viewfinder images. The area of overlap can be displayed to the user using the indicators described herein.

Figure 5B:
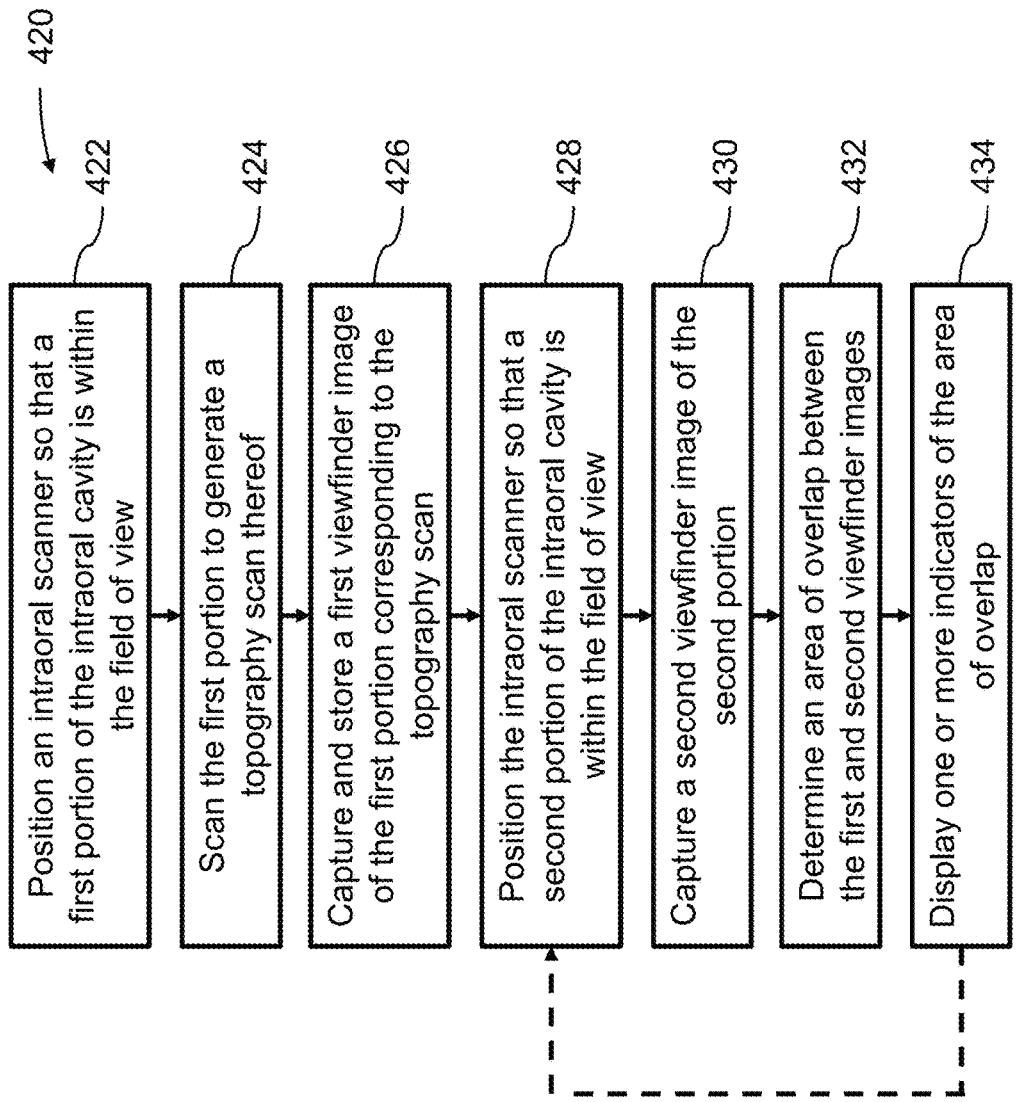
FIG. 5B illustrates a method for determining overlap between a current viewfinder image and previous scanning cover, in accordance with many embodiments.

FIG. 5B illustrates a method 420 for determining overlap between a current viewfinder image and previous scanning coverage, in accordance with many embodiments. The steps of the method 420 can be practiced in combination with or in place of any of the steps of the other methods presented herein, such as the method 400.

In step 422, an intraoral scanner is positioned so that a first portion of an intraoral cavity is within the field of view of the scanner.

In step 424, the first portion is scanned in order to generate a topography scan thereof. The topography scan can be performed using any suitable method, such as the approaches previously described herein. In embodiments where the intraoral scanner is a point-and-shoot scanner, a user input may be required in order to trigger the scan event. Alternatively, a continuous scanner may allow for multiple scan events without requiring a user input to initiate each event, such that the scanning of the first portion is performed automatically or semi-automatically. The resultant topography scan data can be stored a suitable location (e.g., in the memory 240 of the system 200).

In step 426, a first viewfinder image of the first portion corresponding to the topography scan is captured and stored (e.g., in the memory 240 of the system 200). Optionally, the first viewfinder image can be a composite color image produced from a plurality of monochromatic images generated using different illumination wavelengths, as described herein. The step 426 can be performed simultaneously with the step 424, such that the viewfinder image is recorded simultaneously with the topography scan. Alternatively, the step 426 can be performed prior to or after the step 424, such that the viewfinder image is recorded at a different time than the topography scan. In many embodiments, the time interval between the steps 424 and 426 is sufficiently short such that the scanner remains in approximately the same position and orientation for the topography scanning and viewfinder imaging, thereby ensuring that the first viewfinder image provides an accurate representation of the coverage of the topography scan.

In step 428, the intraoral scanner is positioned so that a second portion of the intraoral cavity is within the field of view. The second portion may overlap wholly or in part with the first portion. Alternatively, the two portions may be entirely separate with no overlapping areas.

In step 430, a second viewfinder image of the second portion is captured, in accordance with the embodiments presented herein.

In step 432, an area of overlap between the first and second viewfinder images is determined. Any suitable device can be used to determine the overlap, such as the processing unit 230 of the system 200. Various techniques can be used to determine the area of overlap. For example, suitable algorithms can be used to register the first and second viewfinder images to each other, such as image mosaicing algorithms or other techniques known to those of skill in the art. In many embodiments, a feature-based method can be implemented in order to register the images. For example, the image data can be analyzed to identify one or more features present in both the viewfinder image and the reference images. Suitable features can comprise points, corners, edges, boundaries between two colors, and the like. Accordingly, the images can be registered based on identification and matching of corresponding features. Alternatively or in combination, the image registration can be performed using an intensity-based method. For example, an intensity-based method can comprise determining, based on the pixel intensities of the images, transformations and/or deformations of the viewfinder image that would place it in the greatest similarity (e.g., based on a suitable similarity measure) with the reference images. Accordingly, the images can be registered by transforming and/or deforming the viewfinder image such that its similarity to the reference images is increased.

Following image registration, the area of overlap can be determined. The area of overlap can comprise a plurality of discontinuous areas, such that the overall area is computed as the sum of the discontinuous areas. Alternatively, the area of overlap can comprise a single continuous area. The area of overlap can encompass the entire viewfinder image, for example, if the second viewfinder image is completely overlapped by the first viewfinder image. The area of overlap can be zero, for example, if there is no overlap between the first and second viewfinder images. The area of overlap can be digitally represented by any suitable method. For example, a suitable algorithm can be used to compute a set of pixel coordinates representing the boundary of the area of overlap with respect to the second viewfinder image. Alternatively or in combination, the area can be represented as one or more of straight lines, curved lines, or a polygon or other suitable shape.

In step 434, the one or more indicators of the area of overlap are displayed (e.g., on a screen or monitor of the display 220). The indicators can be presented as a graphical overlay on the second viewfinder image, such that the user can visually identify areas of the second viewfinder image that were covered in the topography scan, as described herein.

In many embodiments, the steps 428, 430, 432, and 434 can be repeated, as indicated by the dashed line in FIG. 5B, thereby updating the displayed viewfinder image and indicators as the scanner is moved through a plurality of different positions relative to the intraoral cavity. At each position, the area of overlap between the current viewfinder image and the first viewfinder image is calculated, thereby allowing the user to observe the extent to which the current viewfinder image overlaps with the generated topography scan.

A scanning procedure may comprise positioning the scanner at various locations relative to the patient's intraoral cavity in order to collect multiple topography scans. In many embodiments, a viewfinder image is recorded for each corresponding topography scan, and the current viewfinder image is compared to all of the stored viewfinder images in order to determine the overlap between the current field of view and all previous topography scans. This approach can allow the user to track scanning progress for the entire procedure, thereby improving flexibility and user convenience. In alternative embodiments, the current viewfinder image may be compared to only a subset of the stored viewfinder images. For example, the current viewfinder image may be compared to a stored viewfinder image corresponding to the most recent topography scan(s). This approach may be advantageous in terms of reducing the amount of computation and processing time needed to determine the area of overlap.

Figure 5C:
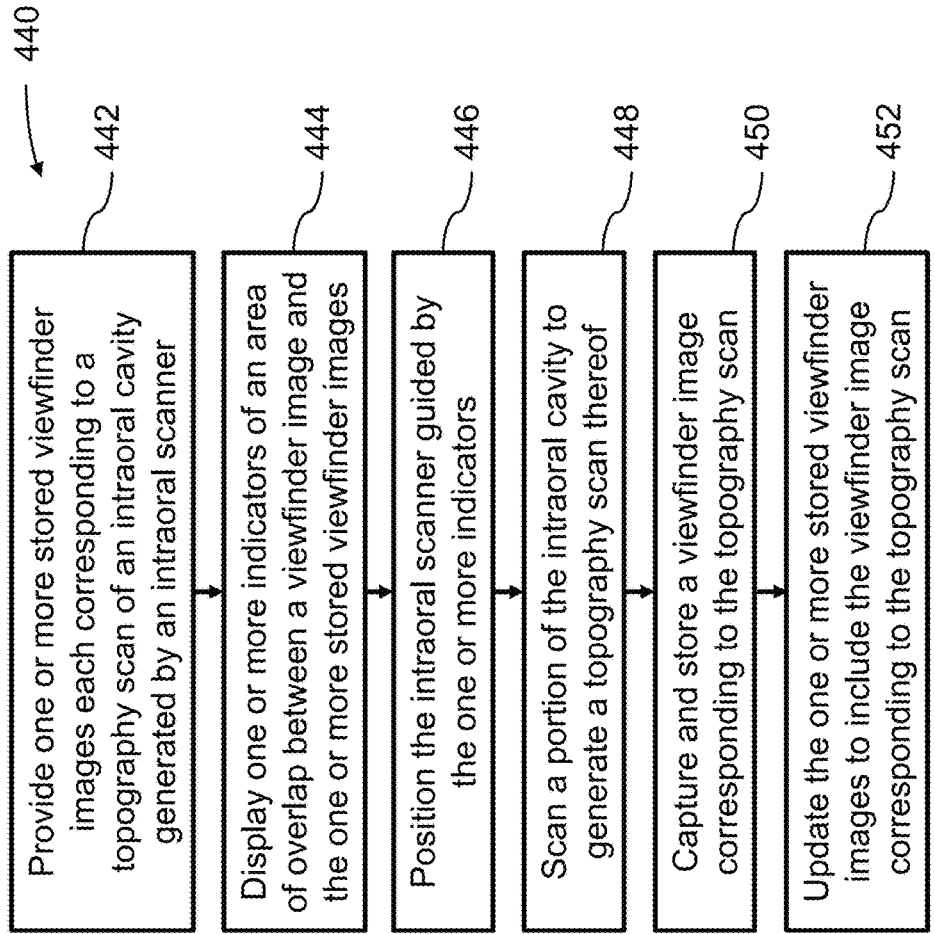
FIG. 5C illustrates a method for tracking scanning progress, in accordance with many embodiments.

FIG. 5C illustrates a method 440 for tracking scanning progress, in accordance with many embodiments. The steps of the method 440 can be practiced in combination with or in place of any of the steps of the other methods presented herein, such as the method 400 or the method 420.

In step 442, one or more stored viewfinder images are provided, each corresponding to a topography scan of an intraoral cavity generated by an intraoral scanner. The stored viewfinder images can be any suitable set of images corresponding to previously scanned portions of the intraoral cavity and can be stored in a suitable device (e.g., memory 240). In many embodiments, the stored viewfinder images are images recorded by the viewfinder in conjunction with previous topography scans, as previously described herein. As discussed above, the stored viewfinder images may comprise a plurality of images taken during the entire scanning procedure, or may comprise only a single image corresponding to a single previous topography scan (e.g., the immediately preceding scan). Optionally, the stored viewfinder images can comprise at least one composite image produced by registering and merging a series of previously recorded viewfinder images with each other (e.g., an image mosaic), such that the composite image corresponds to the scanning coverage over a plurality of previous scans.

In step 444, one or more indicators of an area of overlap between a viewfinder image and the one or more stored viewfinder images are displayed. The indicators can be displayed to the user as a graphical overlay on a viewfinder image corresponding to the current field of view of the intraoral scanner. The indicators can be generated based on a determined area of overlap between the stored viewfinder images and the currently displayed viewfinder image, using any of the techniques previously described herein. Alternatively, in embodiments where the indicators are generated and updated at a rate different from the viewfinder video rate, the indicators can be generated based on a determined area of overlap between the stored viewfinder images and a viewfinder image different than the currently displayed viewfinder image (e.g., a viewfinder image captured one or more frames prior to the currently displayed viewfinder image). In many embodiments, the viewfinder image used for the overlap calculation is the same as or similar to currently displayed viewfinder image such that the displayed indicators provide an accurate representation of the previous scan coverage.

In step 446, the intraoral scanner is positioned guided by the one or more indicators. In many embodiments, the indicators are updated as the intraoral scanner is moved so as to accurately reflect the extent of scanning coverage relative to the current viewfinder image. As described herein, the user can use the indicators to determine which portions of the intraoral cavity have already been scanned and aim the scanner device accordingly.

In step 448, a portion of the intraoral cavity is scanned to generate a topography scan thereof, as described herein.

In step 450, a viewfinder image corresponding to the topography scan is captured and stored, as described herein. The step 450 may occur concurrently with, prior to, or after the step 448. The viewfinder image can be stored in the same location as the one or more stored viewfinder images (e.g., memory 240).

In step 452, the one or more stored viewfinder images are updated to include the viewfinder image corresponding to the topography scan. Accordingly, if the method 440 is subsequently repeated, the area of overlap in step 444 can be determined using the updated set of stored viewfinder images. The method 440 can be used to update the displayed indicators as new topography scans are acquired, therefore providing tracking of scanning progress. In embodiments where only a single previous viewfinder image is stored, the update step involves replacing the previously viewfinder image with the newly recorded viewfinder image of step 450. In alternative embodiments where the stored viewfinder images comprise a plurality of previous viewfinder images, the updating step involves adding the viewfinder image of step 450 to the set of stored viewfinder images.

Figure 6A:
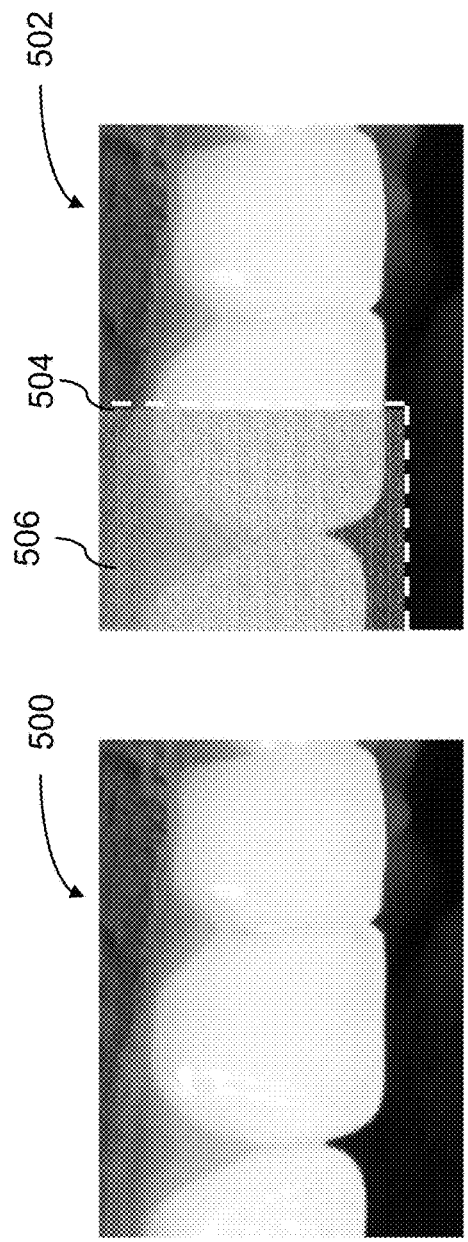
FIGS. 6A through 6C illustrate viewfinder images with overlaid indicators, in accordance with many embodiments.
Figure 6B:
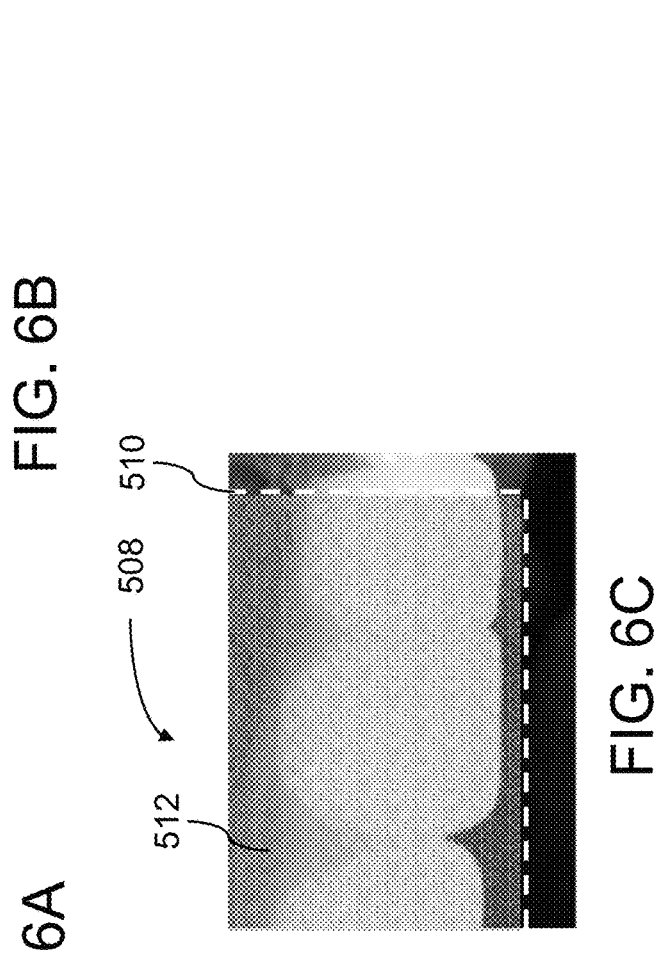
Figure 6C:
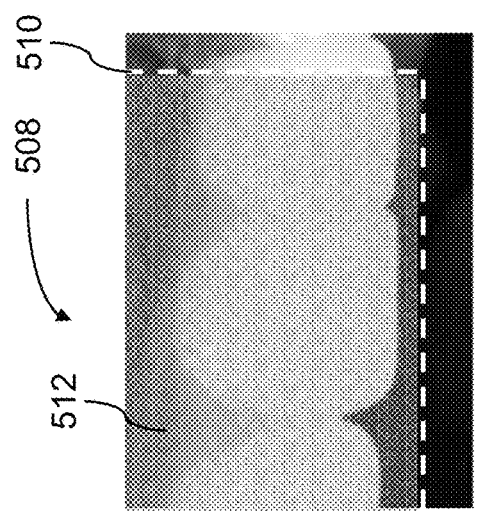

FIGS. 6A through 6C illustrate viewfinder images with overlaid indicators, in accordance with many embodiments. FIG. 6A illustrates a viewfinder image 500 of an intraoral cavity portion prior to acquisition of any scan data of that portion. Since no scan data has been obtained, the viewfinder image 500 does not include any overlaid indicators.

FIG. 6B illustrates a viewfinder image 502 after a first topography scan covering part of the intraoral cavity portion has been performed. The image 502 includes overlaid graphical indicators, including a dashed line 504 marking a boundary of the area of overlap between the current field of view and the first topography scan coverage, as well as shading 506 spanning the area of overlap. Alternatively or in combination, the indicators can comprise other graphical elements, such as one or more of an alphanumerical value, symbol, line, shape, or the like, as well as coloring, shading, blurring, texturing, or other feature(s) of the area of overlap suitable to distinguish it from the non-overlapping portions of the viewfinder image. FIG. 6C illustrates a viewfinder image 508 after a second topography scan covering additional parts of the intraoral cavity portion has been performed. The dashed line 510 and shading 512 correspond to the coverage of the first and second topography scans combined. The dashed line 510 and shading 512 cover a larger area of the viewfinder image 508 compared to FIG. 6B, indicating that the area of previous scan coverage has increased.

Figure 7:
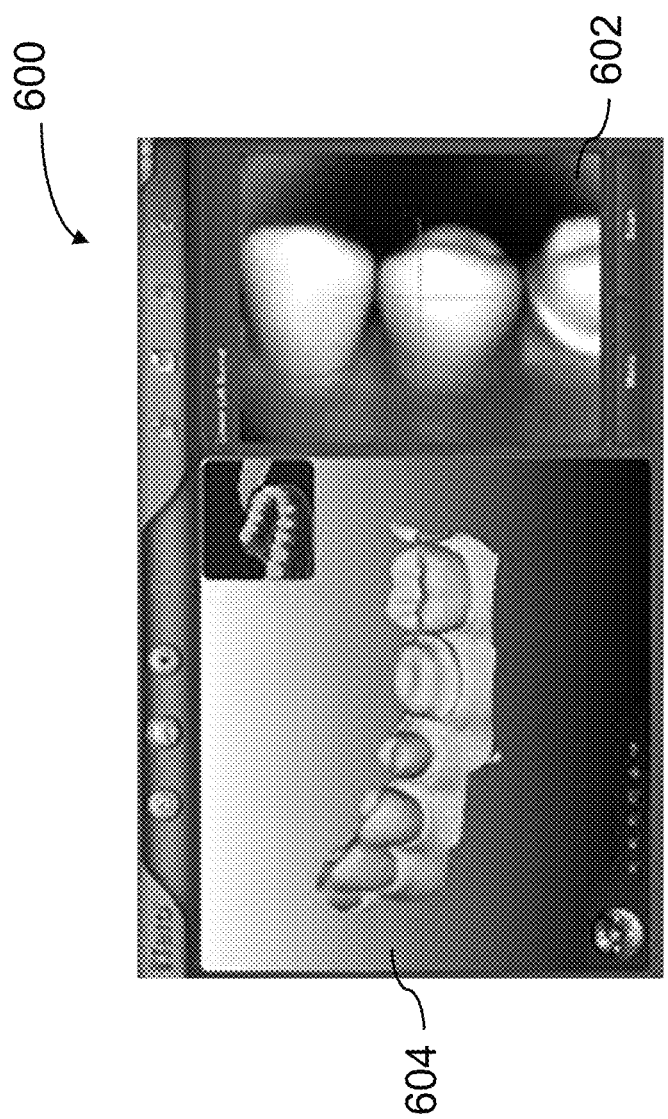
FIG. 7 illustrates a user interface suitable for use with an intraoral scanning system, in accordance with many embodiments.

FIG. 7 illustrates a user interface 600 suitable for use with an intraoral scanning system, in accordance with many embodiments. The user interface 600 can be presented to a user on a suitable display (e.g., display 220). In many embodiments, the user interface 600 comprises a viewfinder window 602 used to display viewfinder image data corresponding to the field of view of the intraoral scanner. The viewfinder window 602 can provide a real-time or approximately real-time video stream of the viewfinder image data. As described herein, visual indicators (not shown) can be overlaid onto the viewfinder images displayed in the viewfinder window 602 so as to allow the user to identify previously scanned portions of the intraoral cavity. Optionally, the user interface 600 can also comprise a separate scanning window 604 used to present surface topography data obtained during the scanning procedure, e.g., as a three-dimensional virtual model. In alternative embodiments, the scanning window 604 can be presented on a separate display from the viewfinder window 602. Suitable control commands can be used to manipulate the virtual model in the scanning window 604 (e.g., zoom in, zoom out, rotate, translate), such as control commands generated based on user input (e.g., via the input unit 210). In many embodiments, the virtual model can be updated in real time so that the user can immediately see the results of the latest scan. Thus, during the scanning procedure, the user can ensure satisfactory scan overlap and coverage, guided at least in part by current viewfinder image and one or more indicators of the viewfinder window 602, and also verify scanning progress, based at least in part on the reconstructed surface topography of the virtual model of the scanning window 604.

The various techniques described herein may be partially or fully implemented using code that is storable upon storage media and computer readable media, and executable by one or more processors of a computer system. The processor can comprise array logic such as programmable array logic (hereinafter PAL), configured to perform the techniques described herein. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for guiding scanning of an intraoral cavity of a patient, the method comprising:
    capturing, using imaging optics, a first viewfinder image of a first portion of the intraoral cavity of the patient, the first viewfinder image including a viewfinder view that correspond to an intraoral scanner view;
    capturing, using the imaging optics, topography data of the first portion of the intraoral cavity and corresponding to the first viewfinder image by measuring one or more characteristics of returning light beams, having passed through the imaging optics and having been reflected off surfaces within the intraoral cavity;
    capturing a second viewfinder image of a second portion of the intraoral cavity;
    displaying the second viewfinder image; and
    displaying one or more visual indicators on the second viewfinder image corresponding to coverage of the topography data.

2. The method of claim 1, wherein the one or more visual indicators includes coloring or shading of the coverage of the topography data.

3. The method of claim 1, wherein the one or more visual indicators move when a user adjusts the portion of the intraoral cavity within the field of view of the intraoral scanner in order to allow the user to position the field of view of the intraoral scanner.

4. The method of claim 1, further comprising scanning the portion of the intraoral cavity with the one or more visual indicators displayed at one or more locations on a display.

5. The method of claim 1, wherein a third or more viewfinder images are displayed with the visual indicators.

6. The method of claim 1, further comprising:
    determining the area of overlap of the second viewfinder image with the first viewfinder image, comprising comparing the first viewfinder image to the second viewfinder image; and
    wherein one of the one or more visual indicators indicates the overlap of the first viewfinder image with the second viewfinder image.

7. The method of claim 6, wherein determining the area of overlap of the second viewfinder image with the first viewfinder image includes:
    registering the second viewfinder image to the first viewfinder image.

8. The method of claim 7, wherein registering the second viewfinder image to the first viewfinder image comprises identifying one or more features present in both the second viewfinder image and the first viewfinder image.

9. The method of claim 7, wherein registering the second viewfinder image to the first viewfinder image comprises at least one of transforming or deforming the second viewfinder image to increase its similarity to the first viewfinder image.

10. The method of claim 5, wherein the one or more visual indicators comprise a warning indicator if the area of overlap is smaller than a predetermined amount.

11. The method of claim 1, further comprising:
    positioning an intraoral scanner within the intraoral cavity, the positioning being guided at least in part by the one or more visual indicators.

12. The method of claim 11, further comprising:
    recording a viewfinder image corresponding to the topography data while capturing the topography data of the first portion of the intraoral cavity with the intraoral scanner; and
    updating the first viewfinder image to include the recorded viewfinder image.

13. A system for guiding scanning of an intraoral cavity of a patient, the system comprising:
    an intraoral scanner comprising an optical assembly and configured to capture topography data of a first portion of the intraoral cavity by measuring one or more characteristics of returning light beams, having passed through the optical assembly and having been reflected by surfaces within the intraoral cavity;
    a viewfinder optically aligned with the optical assembly of the intraoral scanner in order to capture a first viewfinder image;
    a display configured to display one or more visual indicators on one or more locations of the display in order to provide guidance for positioning the intraoral scanner; and
    a processing unit operatively coupled to the intraoral scanner, the display, and the viewfinder, the processing unit comprising instructions to generate the one or more visual indicators on a second viewfinder image, the visual indicators corresponding to coverage of the topography data.

14. The system of claim 13, wherein the intraoral scanner is configured for point-and-shoot scanning.

15. The system of claim 13, wherein the intraoral scanner is configured for continuous scanning.

16. The system of claim 13, further comprising instructions to determine an area of overlap and for registering the first viewfinder image to the second viewfinder image.

17. The system of claim 16, wherein the instructions for registering the first viewfinder image to the second viewfinder image comprises instructions for identifying one or more features present in both the first viewfinder image and the second viewfinder image.

18. The system of claim 16, wherein the instructions for registering the first viewfinder image to the second viewfinder image comprises instructions for transforming or deforming the first viewfinder image to increase its similarity to the second viewfinder image.

19. The system of claim 13, wherein the one or more visual indicators comprise a coloring of the coverage of the topography data.

20. The system of claim 13, wherein the one or more visual indicators comprise a warning indicator if the area of overlap is smaller than a predetermined amount.

\* \* \* \* \*